US00RE34090E

United States Patent [19]

Seyedin et al.

[11] E Patent Number: Re. 34,090

[45] Reissued Date of Patent: Oct. 6, 1992

[54] POLYPEPTIDE CARTILAGE-INDUCING FACTORS FOUND IN BONE

[75] Inventors: Saeid Seyedin, Saratoga, Calif.; Thomas Thomas, West Roxbury, Mass.; Hanne Bentz, Newark, Calif.; Larry Ellingsworth, San Jose, Calif.; Rosa Armstrong, Palo Alto, Calif.

[73] Assignee: Celtrix Laboratories, Inc., Santa Clara, Calif.

[21] Appl. No.: 664,762

[22] Filed: Mar. 5, 1991

Related U.S. Patent Documents

Reissue of:

[64] Patent No.. 4,810,691
Issued: Mar. 7, 1989
Appl. No.: 131,209
Filed: Dec. 10, 1987

U.S. Applications:

[60] Division of Ser. No. 129,864, Sep. 27, 1988, Pat. No. 4,774,322, which is a division of Ser. No. 767,144, Aug. 19, 1985, abandoned, which is a continuation-in-part of Ser. No. 630,938, Jul. 16, 1984, abandoned.

[51] Int. Cl.[5] ..... A61K 37/02; C07K 3/28

[52] U.S. Cl. ..... 514/2; 514/12; 514/21; 530/841

[58] Field of Search ..... 514/2, 12, 21; 530/841

[56] References Cited

U.S. PATENT DOCUMENTS

| | | | |
|---|---|---|---|
| 3,458,397 | 7/1969 | Meyers | 435/268 |
| 4,294,753 | 10/1981 | Urist | 530/841 |
| 4,394,370 | 7/1983 | Jefferies | 424/15 |
| 4,434,094 | 2/1984 | Seyedin et al. | 530/21 |
| 4,455,256 | 6/1984 | Urist | 530/21 |

FOREIGN PATENT DOCUMENTS

| | | |
|---|---|---|
| 0128849 | 6/1984 | European Pat. Off. . |
| WO84/01106 | 3/1984 | PCT Int'l Appl. . |

OTHER PUBLICATIONS

Roberts et al., "Transforming Growth Factor Type B: Rapid Induction of Fibrosis and Angiogenesis In Vivo and Stimulation of Collagen Formation In Vitro", Proc. Natl. Acad. Sci. USA, vol. 83, pp. 4167–4171, Jun. 1986, vol. 233, pp. 532–534, Aug. 1986.

Anzano, M. A., *Proc Nat Acad Sci USA* (1983) 80:6264–68.

Assoian, R. et al., *J Biol Chem* (1983) 258:7155–60.

Seyedin, S., *J Biol Chem* (1986) 261:5693–95.

Sporn et al., "Transforming Growth Factor-B: Biological Function and Chemical Structure", Science, vol. 233, pp. 532–534, Aug. 1986.

*Primary Examiner*—Nathan M. Nutter
*Attorney, Agent, or Firm*—Morrison & Foerster

[57] ABSTRACT

Two proteins that are found is bone and that have in vivo chondrogenic/osteogenic activity in combination with a co-factor are described. Both proteins also were active in combination with EGF in the in vitro TGF-$\beta$ assay. Each has a molecular weight of approximately 26,000 daltons by SDS-PAGE. Each is reduced to a single polypeptide indicating that the proteins are probably homodimers. One has an N-terminal sequence identical to that of human placenta-derived TGF-$\beta$ whereas the other has an N-terminal sequence that is different from that of TGF-$\beta$ derived from human placenta. The two proteins may be purified to homogeneity using RP-HPLC or acetic acid-urea gel electrophoresis.

5 Claims, 7 Drawing Sheets

POLYPEPTIDE CARTILAGE-INDUCING FACTORS FOUND IN BONE

Matter enclosed in heavy brackets [ ] appears in the original patent but forms no part of this reissue specification; matter printed in italics indicates the additions made by reissue.

CROSS-REFERENCE TO RELATED APPLICATION

This application *reissue application of application Ser. No. 131,209, filed Dec. 10, 1987, now U.S. Pat. No. 4,810,691, which* is a division of application Ser. No. 129,864, filed Sep. 27, 1988, now U.S. Pat. No. 4,774,322, which is a division of application Ser. No. 767,144, filed Aug. 19, 1985, now abandoned, which is a continuation-in-part of copending U.S. Ser. No. 630,938, filed Jul. 16, 1984 and now abandoned.

DESCRIPTION

1. Technical Field

The present invention relates to protein chemistry. More particularly, it relates to polypeptides that are involved in cartilage induction in vivo. These polypeptides are sometimes referred to as cartilage-inducing factors (CIFs) herein.

2. Background

Parent U.S. patent application Ser. No. 630,938 describes two proteins that were isolated from bovine bone. These proteins exhibited in vitro chondrogenic activity. Further characterization and testing of these two proteins revealed that one of them may be the same polypeptide as a human placenta-derived polypeptide called "beta type transforming growth factor" (TGF-$\beta$) and described in International patent application No. PCT/US83/01460 published Mar. 29, 1984 under No. WO 84/01106 and EPA No. 84450016.5 published Dec. 19, 1984 under No. 0128849. The other has a different partial amino acid sequence than that reported for the human Placenta-derived TGF-$\beta$, but is active in the same anchorage-independent cell growth assay as was used to characterize the biological activity of TGF-$\beta$.

There have been prior attempts to identify and isolate factors in bone that are involved in stimulating bone growth. U.S. Pat. No. 4,294,753 to Urist reports the preparation of a crude "bone morphogenic protein" by extracting demineralized bone with urea or guanidine hydrochloride and reprecipitating protein from the extract. Urist subsequently reported (Urist M. R., Clin Orthop Rel Res (1982) 162:219) that ion exchange purification of this crude protein mixture yielded an activity that was unadsorbed to carboxymethylcellulose (CMC) at pH 4.8. Urist's most recent reports (Science (1983) 220:680–685 and Proc Natl Acad Science (USA) (1984) 81:371–375) describe BMPs having molecular weights of 17 and 18,500 daltons.

U.S. Pat. No. 4,434,094 reports the partial purification of a bone generation-stimulating, bone-derived protein factor by extraction with chaotropic agents, fractionation on anion and cation exchange columns, and recovery of the activity from a fraction adsorbed to CMC at PH 4.8. This new protein fraction was termed "osteogenic factor" (OF) and was characterized as having a molecular weight below about 30,000 daltons and as tracking the purification process described. The proteins of the current invention were purified to homogeneity using a purification procedure that is similar in part to that disclosed in U.S. Pat. No. 4,434,094.

DISCLOSURE OF THE INVENTION

The invention provides two CIFs found in mammalian bone that:

(1) are co-factors for inducing cartilage formation in vivo.

(2) promote connective tissue deposition in vivo in the absence of any added activating agent or co-factor, and (3) are active in the anchorage-independent cell growth assay used to characterize TGF-$\beta$ (this assay is sometimes called the "TGF-$\beta$ assay" herein and is described in Methods for preparation of Media, Supplements, and Substrata for Serum-Free Animal Cell Culture (1984) pp 181–194, Alan R. Liss Inc.). These two polypeptides are called CIF-A and CIF-B, respectively, herein.

The invention further provides a process for obtaining CIF-A and CIF-B in substantially pure form from bone. In this regard the presence in bone of proteins having activity in the RGF-$\beta$ assay has not been reported previously. CIF-A has a partial (30 amino acids) N-terminal amino acid sequence that is the same as the partial N-terminal sequence reported for human Placenta-derived TGF-$\beta$. But lacking total sequencing of both molecules, it is not known whether they are the same polypeptide. CIF-B has a different partial (30 amino acids) N-terminal amino acid sequence. The invention further provides compositions and methods for promoting proliferation of cells and for promoting connective tissue deposition using the CIFs.

Accordingly, one aspect of the invention is a polypeptide that: (a) is found in mammalian bone, (b) is a co-factor for inducing cartilage information, (c) is active in the TGF-$\beta$ assay, (d) is a dimer of approximately 26,000 daltons as determined by SDS-PAGE, and (e) is substantially pure.

The process for isolating the CIFs from bone involves:

(a) extracting demineralized bond (DMB) with a chaotropic (dissociative) extractant that solubilizes non-fibrous proteins;

(b) subjecting the extract from step (a) to gel filtration to recover a fraction containing proteins of molecular weight 10,000–40,000 daltons;

(c) adsorbing the fraction from step (b) onto a carboxymethyl cellulose cation exchanger at approximately pH 4.5–5.5 under denaturing conditions;

(d) eluting the adsorbed fraction from the cation exchanger with a sodium chloride gradient;

(e) subjecting the portion of the eluate from step (d) that elutes at approximately 150 to 250 mM sodium chloride to reverse phase high performance liquid chromatography (RP-HPLC) or a nondenaturing gel electrophoresis; and (f) recovering the CIFs from the RP-HPLC or gel electrophoresis.

The composition for promoting proliferation of normal animal cells comprises:

(a) at least one of the above-described polypeptides;

(b) a TGF-$\beta$ activating agent; and (c) a pharmaceutically acceptable carrier, the polypeptide and activating agent being present in amounts sufficient to promote cell proliferation.

The method of promoting normal cell proliferation comprises administering an effective amount of the above-described composition to a patient.

The composition for promoting connective tissue deposition comprises:

(a) an effective amount of one or both of the above-described polypeptides substantially free of co-factor or activating agent, and (b) a pharmaceutically acceptable carrier. The method of promoting connective tissue deposition comprises placing the above-described composition at a predetermined site within the body of a patient.

MODES OF CARRYING OUT THE INVENTION

Figure 1:
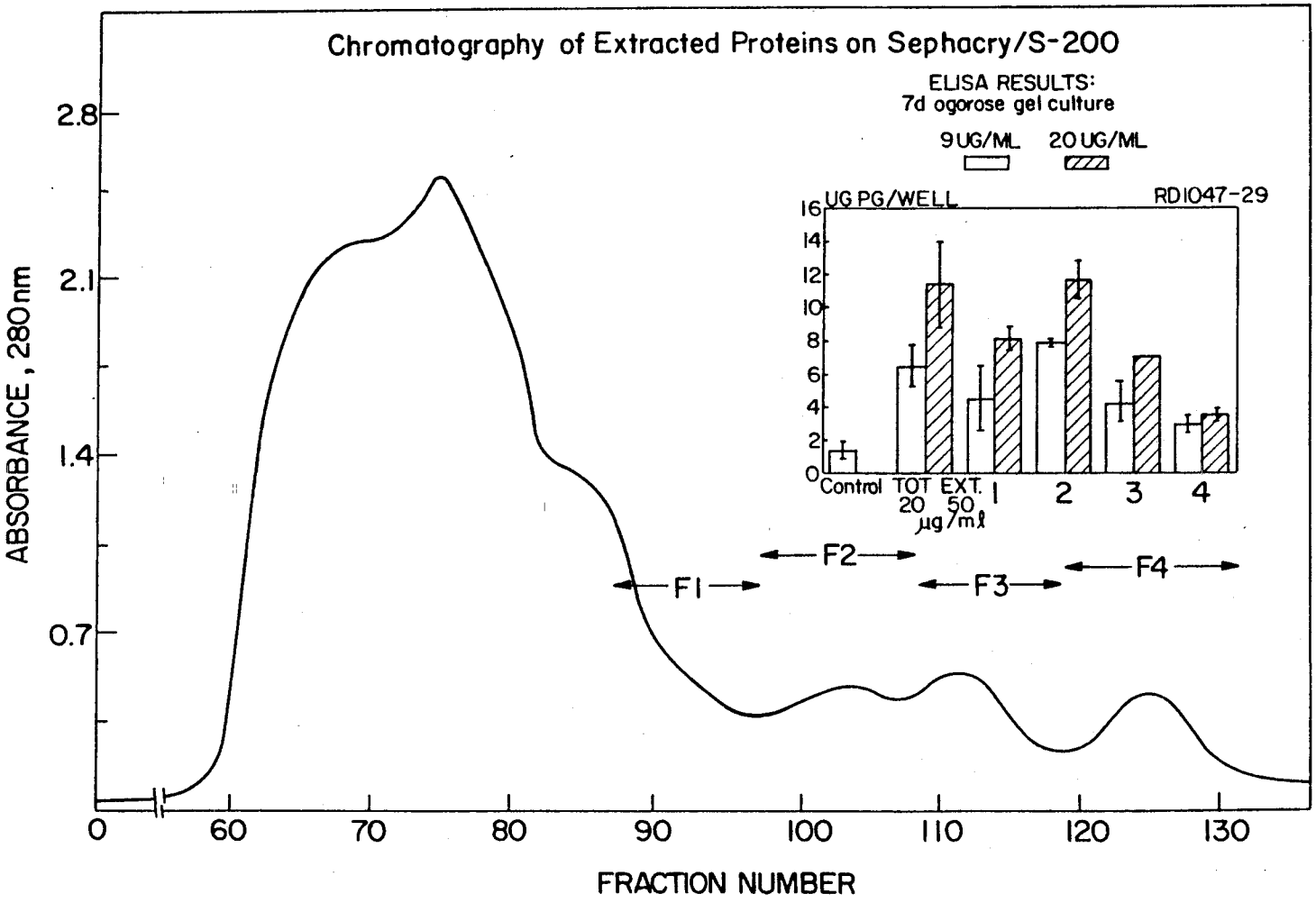
FIG. 1 is a graph of the optical densities (absorbances) (280 nm) and in vitro chondrogenic activities of the gel filtration fractions of the example (section C), infra.

The polypeptides of the invention were isolated from bovine bone. The polypeptides have been only partiallY sequenced at this time. In view of this and since the complete amino acid sequence of TGF-$\beta$ has not been reported, the primary structure relationships between the invention CIFs and TGF-$\beta$s are not known completely. However based on comparisons of partial sequences of N-terminii, molecular weight analyses, apparent secondary structures, and bioloqical activity. CIF-A may be identical or substantially homologous to TGF-$\beta$ derived from human placenta. CIF-A is, however, more prevalent in bone than TGF-$\beta$ is in platelets, placenta, or kidney. Thus, if the two are the same molecule, it appears more likely that the molecule acts as a chondrogenic/osteogenic agent it its native setting rather than as a transforming growth factor.

The CIFs have in vitro chondrogenic activity by themselves, in vivo chondrogenic activity in combination with certain chondrogenic co-factors, in vivo connective tissue deposition activity by themselves, and in vitro TGF-$\beta$ activity in combination with epidermal growth factor (EGF). In view of their chondrogenic activity and the mode of endochondral bone formation, they are also expected to have in vivo osteogenic activity in combination with chondrogenic co-factors.

In view of the showings that bone inductive proteins from human, monkey, bovine and rat are nonspecies-specific in their abilities to produce endochondral bone in xenogeneic implants (Sampath, T. K., et al. Proc Natl Acad Sci (USA) (1983) 80:6591) and that human platelet/human placenta/bovine kidney-derived TGF-$\beta$ is nonspecies-specific between rodents, cattle, and humans, it is believed that the polypeptides of this invention have been highly conserved among mammalian species (i.e., polypeptides from different mammalian species have amino acid sequences that vary, if at all, in one or more amino acid residue additions, deletions, or substitutions that do not affect the nonspecies-specific activity of the molecule adversely). In this regard the term "substantially equivalent" as used to describe a polypeptide is intended to mean polypeptides, whether native or synthetic and regardless of species or derivation, that have the same amino acid sequence as the referenced polypeptide, and polypeptides of substantially homologous (i.e., at least 90% identity in amino acid sequence) but different amino acid sequence, which difference(s) does not affect nonspecies-specific activity adversely. Accordingly, the polypeptides of this invention may be derived from or found in cells or tissue of diverse animal origin or synthesized by recombinant DNA technology. Porcine or bovine long bone are preferred native sources of the polypeptides because of the ready availability of such bone and the abundance of the polypeptides in bone.

A variety of initial preparation procedures are possible when bone is used as a source, but basically the bone is first cleaned using mechanical or abrasive techniques, fragmented, and further washed with, for example, dilute aqueous acid preferably at low temperature, and then defatted by extraction with a lipophilic solvent such as ether or ethyl acetate. The bone is then demineralized by removal of the calcium phosphates in their various forms, usually by extraction with stronger acid. These techniques are understood in the art, and are disclosed for example, in U.S. Pat. No. 4,434,094. The resulting preparation, a demineralized bone, is the starting material for the preparation of the polypeptides of the invention.

The initial extraction is designed to remove the nonfibrous (e.g., non-collagenous) proteins from the demineralized bone. This can be done with the use of chaotropic agents such as guanidine hydrochloride (at least about 4 molar), urea (8 molar) plus salt, or sodium dodecylsulfate (at least about 1% by volume) or such other chaotropic agents as are known in the art (Termine, et al., J. Biol Chem (1980) 255: 9760–9772; and Sajera and Hascall, J. Biol Chem (1969) 244: 77–87 and 2384–2396). The extraction is preferably carried out at reduced temperatures in the presence of a protease inhibitor to reduce the likelihood of digestion or denaturation of the extracted protein. Examples of protease inhibitors that may be included are phenylmethylsulfonylfluoride (PMSF) sodium azide, N-ethyl maleimide (NEM), benzamidine, and 6-aminohexanoic acid. The PH of the medium depends upon the extractant used. The process of extraction generally takes on the order of about 4 hr to one day.

After extraction, the extractant may be removed by suitable means such as dialysis against water, preceded by concentration by ultrafiltration if desired. Salts can also be removed by controlled electrophoresis, or by molecular sieving, or by any other means known in the art. It is also preferred to maintain a low temperature during this process so as to minimize denaturation of the proteins. Alternatively, the extractant need not be removed, but rather the solution need only be concentrated, for example, by ultrafiltration.

The extract, dissolved or redissolved in chaotropic agent is subjected to gel filtration to obtain fractions of molecular weight below about 40,000 daltons, thus resulting in a major enhancement of purity. Gel sizing is done using standard techniques, preferably on a Sephacryl column at room (10°-25° C.) temperature. The low molecular weight fraction is then subjected to ion exchange chromatography using carboxymethyl cellulose (CMC) at approximately PH 4.5-5.2, preferably about 4.8, in the presence of a nonionic chaotropic agent such as urea. Other cation eXchangers may be used, including those derived from polyacrylamide and cross-linked dextran; however cellulosic cation exchangers are preferred. Of course, as in any ion exchange procedure, the solution must be freed of competing ions before application to the column, and is eluted in an increasing salt concentration gradient as is understood in the art. The fraction eluting from CMC at about 150 to 250 mM NaCl contains the CIFs.

The eluate fraction from the cation exchange chromatography is then subjected to RP-HPLC or a non-denaturing gel electrophoresis for final purification. Standard RP-HPLC techniques and gel electrophoresis techniques are used. Exemplified below is a commercially available RP-HPLC column using a commercially prescribed RP-HPLC protocol. This final purification yields the two polypeptides in substantially pure form. "Substantially pure" means that a polYpeptide contains less than about 5% by weight contaminants.

EXAMPLE

Figure 2:
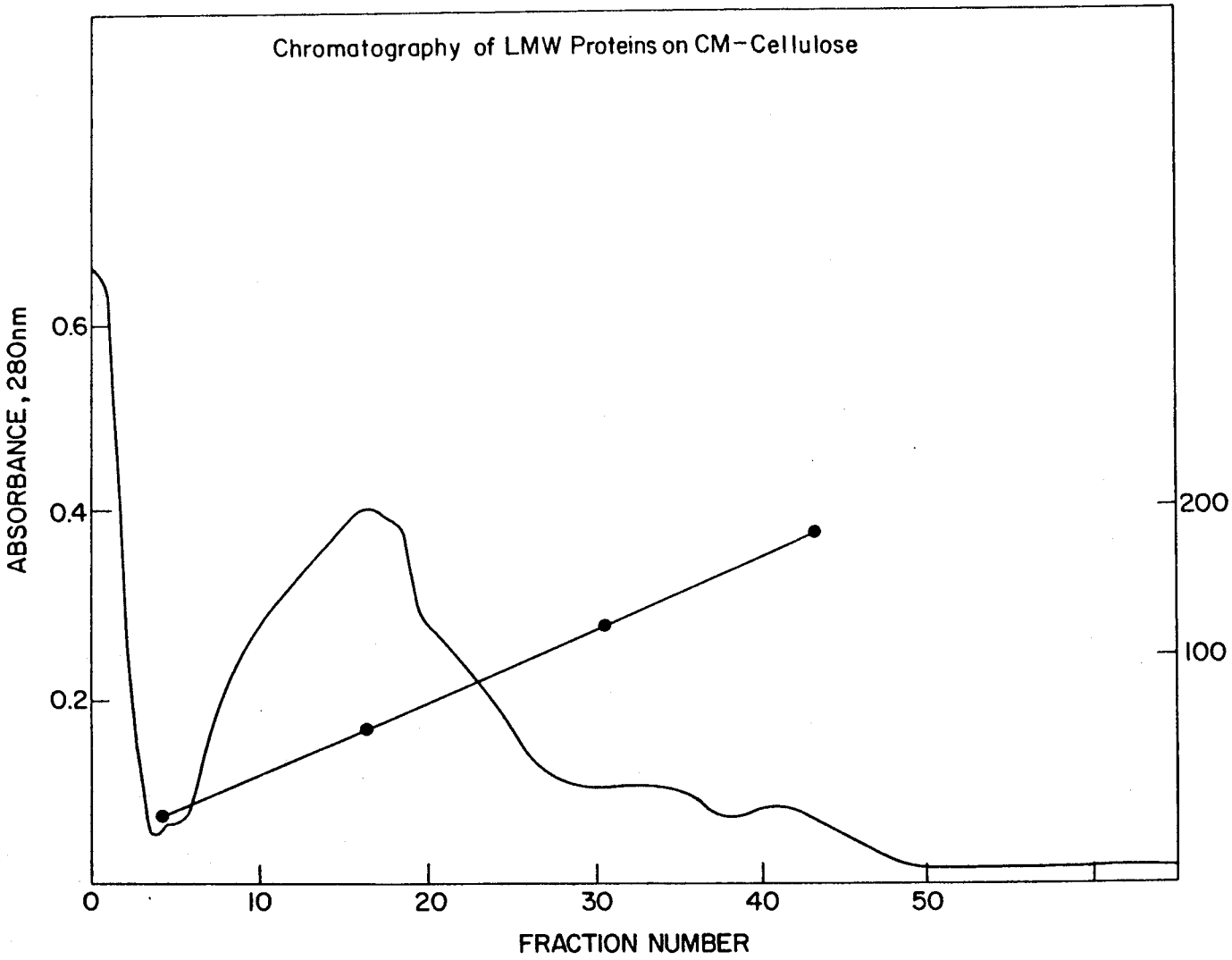
FIG. 2 is a graph of the optical densities (280 nm) of eluate fractions from the preparative ion exchange chromatography of the example (section D), infra.

The following example is intended to illustrate the process for purification as applied to a particular sample. It is not intended to limit the invention. A. Preparation of Demineralized Bone Bovine metatarsal bone was obtained fresh from the slaughterhouse and transported on dry ice. The bones were cleaned of marrow and non-bone tissues, broken in fragments smaller than 1 cm diameter, and pulverized in a mill at 4° C. The pulverized bone was washed twice with 9.4 liters of double distilled water per kg of bone for about 15 min each, and then washed overnight in 0.01N HCl at 4° C. Washed bone was defatted using 3×3 volumes ethanol, followed by 3×3 volumes diethylether, each washed for 20 min. and all at room temperature. The resulting defatted bone powder was then demineralized in 0.5N HCl (25 l/kg defatted bone) at 4° C. The acid was decanted and the resulting DMB washed until the wash pH was greater than 4, and the DMB dried on a suction filter. B. Extraction of Noncollagenous proteins The DMB as prepared in paragraph A was extracted with 3.3 l of 4M guanidine-HCl, 10 mM ethylenediaminetetraacetic acid (EDTA), PH 6.8, 1 mM PMSF, 10 mM NEM per kg for 16 hrs, the suspension suction filtered and the non-soluble material extracted again for 4 hrs. The soluble fractions were combined and concentrated at least 5-fold by ultrafiltration using an Amicon ultrafiltration (10K) unit, and the concentrate dialyzed against 6 changes of 35 volumes cold deionized water over a period of 4 days, and then lyophilized. All of the procedures of this paragraph were conducted at 4° C. except the lyophilization which was conducted under standard lyophilization conditions. C. Gel Filtration The extract from paragraph B, redissolved in 4M guanidine-HCl, was fractionated on a Sephacryl S-200 column equilibrated in 4M guanidine-HCl, 0.02% sodium azide, 10 mM EDTA, PH 6.8. Fractions were assayed by their absorbance at 280 nm and chondrogenic activity by ELISA and the fractions were combined as shown in FIG. 1. Fraction F2 of FIG. 1, constituting a low molecular weight (LMW, 10,000-40,000 daltons) protein fraction possessing the greatest activity was dialyzed against 6 changes of 180 volumes of deionized water and lyophilized. All operations except lyophilization and dialysis (4° C.) were conducted at room temperature. D. Ion Exchange Chromatography Fraction F2 from paragraph C was dissolved in 6M urea, 10 mM NaCl, 1 mM NEM, 50 mM sodium acetate, pH 4.8 and centrifuged at 10,000 rpm for 5 min. The supernatant was fractionated on a CM52 (a commercially available CMC) column equilibrated in the same buffer. Bound proteins were eluted from the column using a 10 mM to 400 mM NaCl gradient in the same buffer, and a total volume of 350 ml at a flow rate of 27 ml/hr. Three major fractions, designated CM-1, CM-2, and CM-3, were collected as shown in FIG. 2. CM-2 and CM-3 eluted at approximately 150-250 mM NaCl. Each fraction was dialyzed against 6 changes of 110 volumes of deionized water for 4 days and lyophilized. All of the foregoing operations were conducted at room temperature except dialysis (4° C.). E. RP-HPLC The lyophilized fractions CM-1 and combined lyophilized fractions CM-2 and CM-3 from $\pi$ D were each dissolved in 0.1% trifluoroacetic acid (TFA) and aliquots of the solutions loaded onto a Vydac C18 RP-HPLC column (4.6 mm ID×25 cm) and washed with 0.1% TFA for 5 min at 1 ml/min. The eluting solvent was a 0%-60% acetonitrile gradient in 0.1% TFA at a rate of 2%/min.

Figure 3:
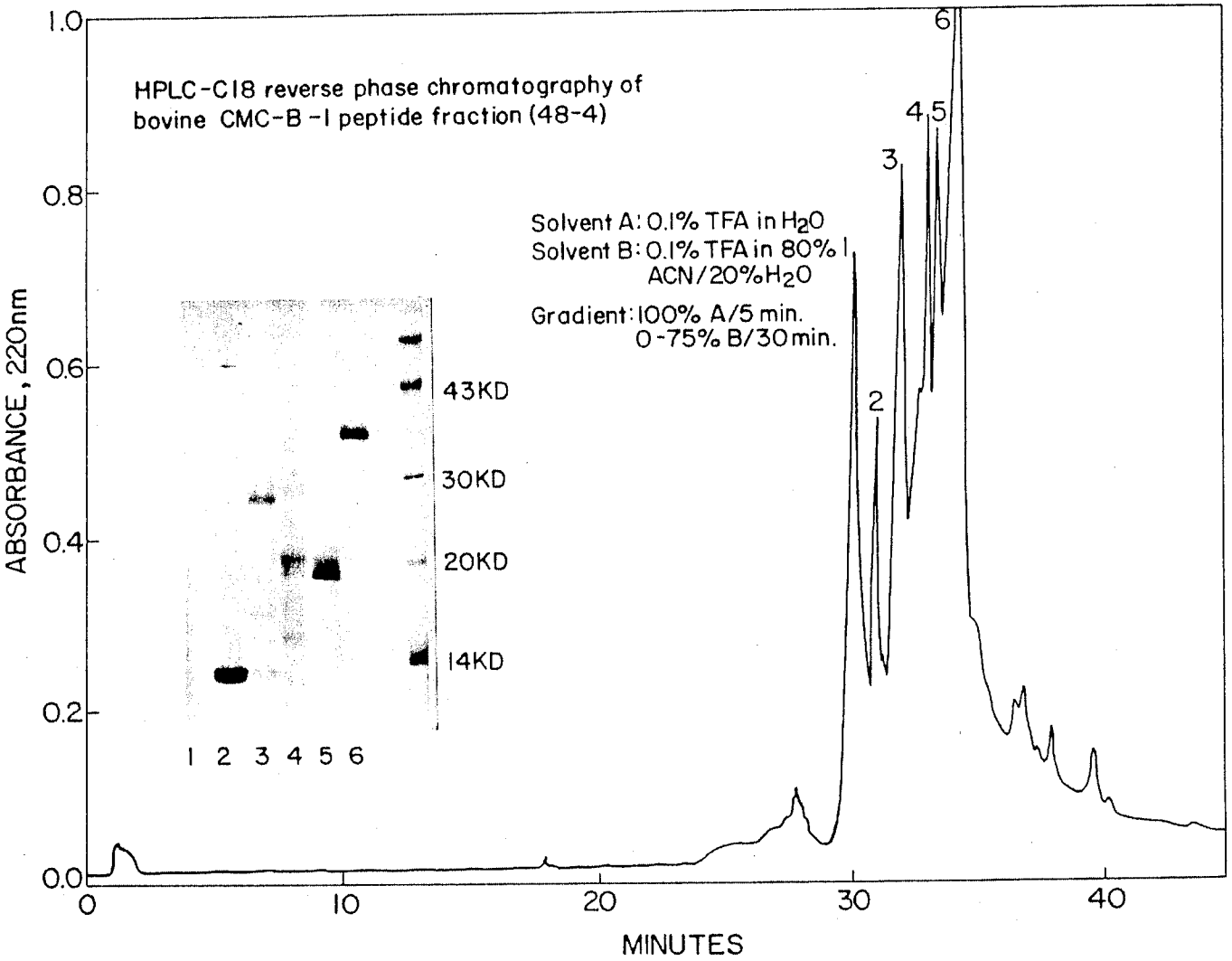
FIG. 3 is a chromatogram and autoradiograph of the SDS-PAGE analysis of the RP-HPLC resolved CM-1 fraction described in section E of the example, infra.

FIG. 3 shows the chromatogram of the RP-HPLC of CM-1. Peak 3 contains predominantly 28 Kd chondrogenic/osteogenic co-factor protein and peak 6 contains predominantly 36 Kd chondrogenic/osteogenic co-factor Protein. Upon rechromatography using the same RP-HPLC system, the two polypeptides were purified to give single bands on 15% SDS-PAGE (analysis also shown in FIG. 3). These protein co-factors are not Part of the present invention and are the subject of a separate, commonly owned U.S. patent application.

Figure 4:
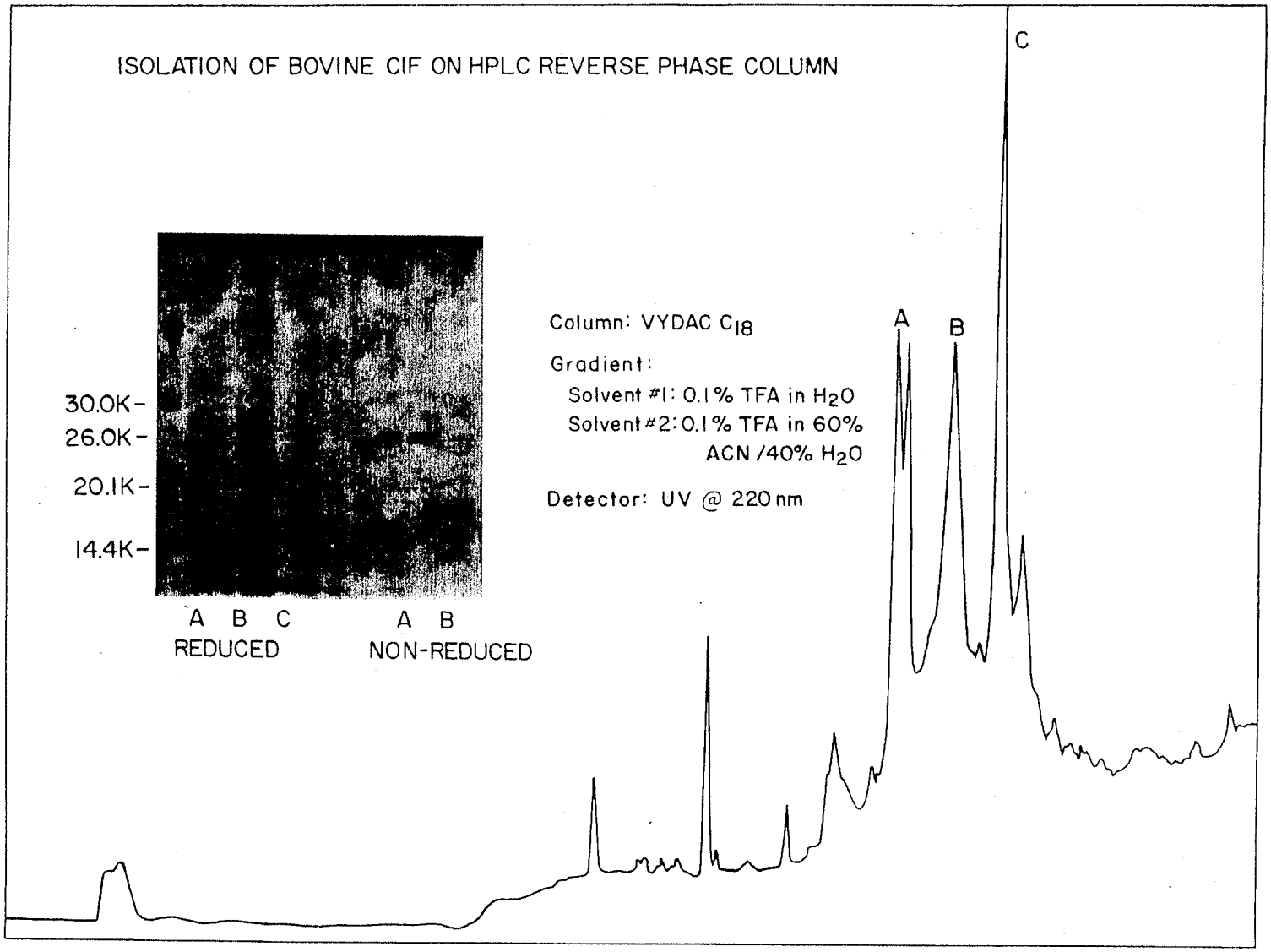
FIG. 4 is a graph of the UV absorbance and electrophoretic profiles of peaks A and B of the preparative RP-HPLC of the example (section E), infra.

Two peaks were obtained from the RP-HPLC of combined CM-2 and CM-3—peak A at about 29.5 min and peak B at about 31.2 min. FIG. 4 shows the absorbance and electrophoretic profiles (reduced and nonreduced) of peaks A and B. The proteins of these peaks were designated CIF-A and CIF-B, respectively.

The proteins were stored in 0.1% TFA/acetonitrile eluting solution at −20° C. until used. F. Alternate purification by Gel Electrophoresis The combined lyophilized fractions CM-2 and CM-3 were fractionated by electrophoresis on an acetic acid-urea gel using the general procedure of Paynim, S. and Chalkley R., Arch Bioch Biophys (1969) 130:337-346. G. Assay for In Vitro Chondrogenic Activity The presence of the desired protein in fractions during purificiation was confirmed using an in vitro assay for the production of cartilage-specific proteoglycans (PG), the identity of which was confirmed by ELISA. This assay is an agarose gel culture model using mesenchymal cells isolated from rat fetal muscle. It assesses the ability of the samples to induce the production of PG. The correlation between in vitro cartilage induction and in vivo bone formation has been shown by Seyedin, S., et al. J Cell Biol (1983) 97:95-1953.

The cell culture was prepared by removing muscle tissue aseptically from the upper limbs of nineteen-day-old Sprague Dawley rat fetuses, mincing the tissue and culturing it in Eagle's Minimum Essential Medium (MEM) with 10% fetal bovine serum (FBS) and 50 units penicillin, 50 μg streptomycin per ml. Cellular outgrowth usually reached confluency within one week, whereupon cells were trypsinized, split 1:2 and used for experimentation within the first three passages.

The cells were placed in agarose gel cultures either with control medium or with samples to be tested. The procedure was basically that of Benya, et al. Cell (1982) 30:215. Briefly, the cell monolayers were harvested by trypsinization, counted on a hemocytometer and resuspended at two times the final cell concentration in the medium with or without the protein fraction to be tested. The control medium was either Hams F-12, Dulbecco's Minimum Essential Medium (DMEM) or CMRL 1066 (Gibco) each containing 10% FBS and antibiotics. The test protein fractions in 0.01N HCl were diluted directly to the desired concentration of test protein diluted with an equal volume with 1% low melting aqarose (Bio-Rad, #162-0017) in F-12, and 0.2 ml of the dilution was plated on 17 mm wells coated with 0.15 ml of 1% high melting (Bio-Rad, #162-0100) agarose. The resulting cultures were incubated at 37° C. for 5 min, chilled at 4° C. for 10 min and then overlayed with 1 ml of the corresponding medium (control or test protein). The cells were then cultured in a humidified atmosphere of 5% $CO_2$, 95% air and fed every 3–4 days thereafter by a complete change with control medium. After 7 days the cultures were frozen and stored at −80° C. before assay.

The cultures were assayed by thawing at 4° C., homogenizing in 4M guanidine-HCl with 50 nM Na acetate, 13 mM EDTA, 6 mM NEM, and 3 nM PMSF at pH 5.8, and extracting by shaking overnight at 4° C. The supernatant fraction from centrifugation at 25,000×g for 40 min at 4° C., was dialyzed overnight at 4° C., against 50 volumes 0.2M NaCl, 50 mM Tris, pH 7.4. The supernatant was assayed for PG bY ELISA as described by Renard, et al. Anal Biochem (1980) 104: 205, and in U.S. Pat. No. 4,434,094.

Briefly, for the ELISA, antiserum to PG was raised in rabbits using standard techniques which showed no cross-reactivity with hyaluronic acid or PG extracted from rat bone. Purified PG (Seyedin, S., et al, supra) from Swarm rat chondrosarcoma tissue was used as standard antigen. The dialyzed samples were diluted 1:1 (v/v) in phosphate-buffered saline (PBS) with 0.05% Tween 20, 1 mg/ml bovine serum albumin (BSA), PH 7.2 for assay. Horseradish peroxidase conjugated goat anti-rabbit IgG (Tago) was the second antibody with o-phenylenediamine as substrate.

Figure 5:
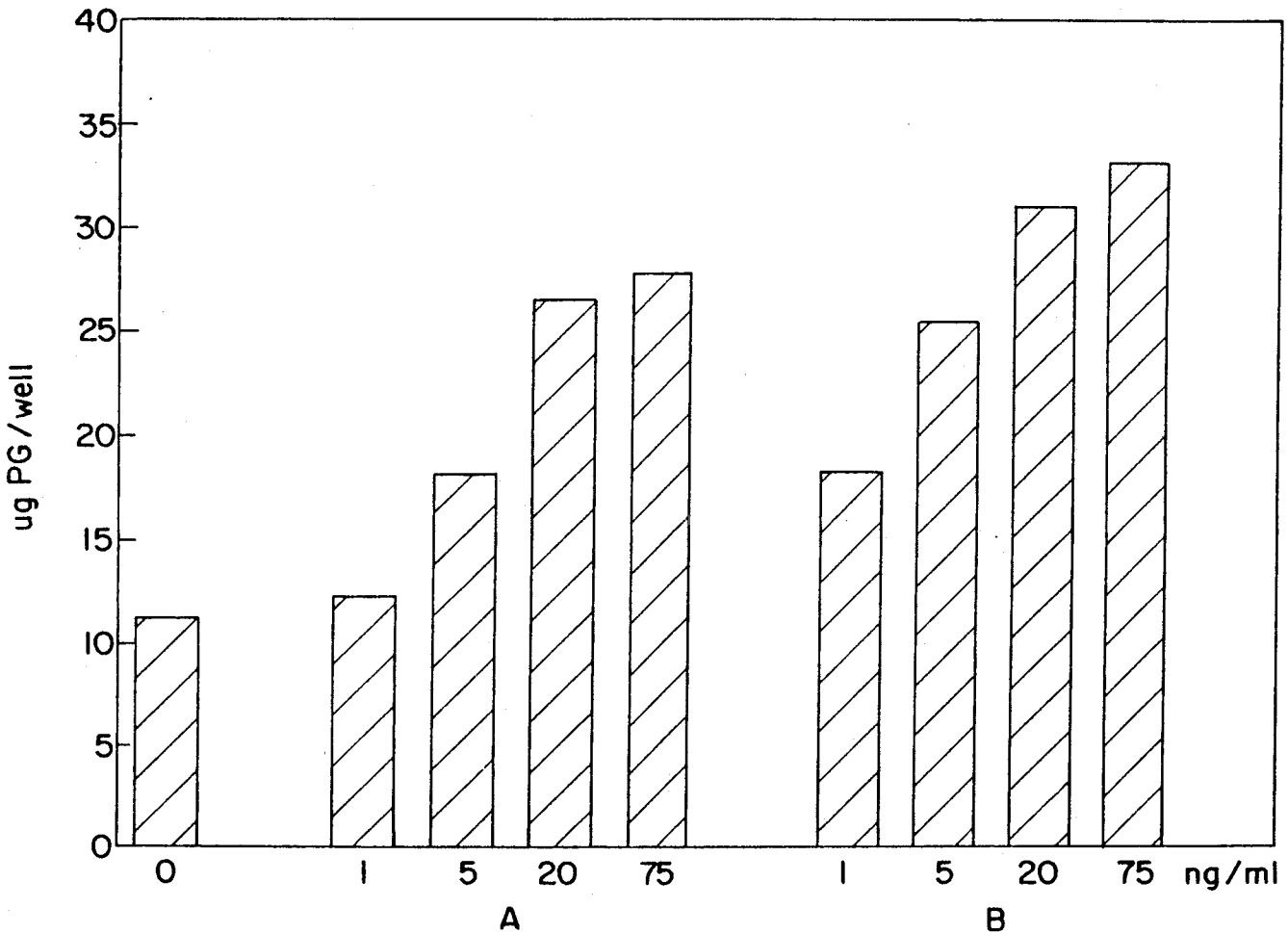
FIG. 5 is a graph of the results of the enzyme-linked immunosorbent assays (ELISAs) for in vitro chondrogenic activity of the proteins of peaks A and B from the RP-HPLC of the example (section E), infra.
Figure 6:
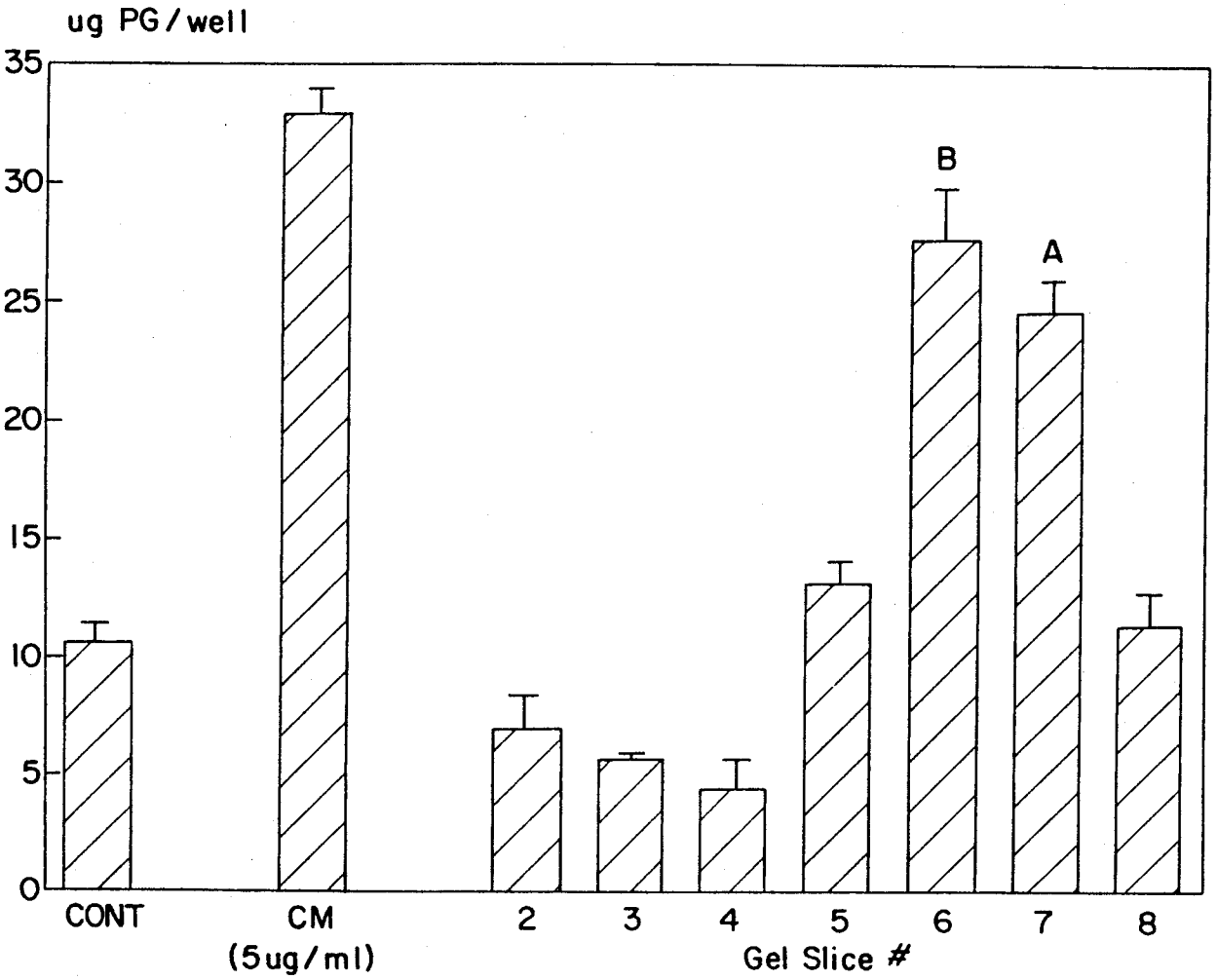
FIG. 6 is a graph of the results of the ELISAs of the acid-urea gel eletrophoresis fractions (section F) of the example, infra.

The results of the ELISA of the RP-HPLC purified CIF-A and CIF-B are shown in FIG. 5. As indicated there, the sensitivity of the assay is within 1 to 5 ng/ml of culture media. The results of the ELISAs on the gel slices of section F are shown in FIG. 6. These results are comparable to the results on CIF-A and CIF-B (corresponding to gel slices 7 and 6) from the RP-HPLC. H. Characterization of the Purified Proteins CIF-A was shown to be a 25,800 dalton protein which on reduction, yielded a 14,800 dalton polypeptide by measurements of the mobilities of the proteins in a 15% Laemmli polyacrylamide gel in SDS (FIG. 4) as described by Laemmli, U. K., et al., Nature (1970) 227:680. It is well understood that molecular weights so determined are approximate and their values are dependent on the method used. The conformation of the protein affects its mobility in this system, and, therefore, the molecular weights obtained will be similar, but not necessarily identical when determined by other procedures. The presence of a single band in the profile of the reduced protein indicates the protein is probably a dimer composed of two polypeptide chains having substantially equivalent amino acid sequences (i.e., it is a homodimer). The discrepancy between the measured weights of dimer and the individual chains is an artifact of the procedure.

CIF-A maintained its activity in the ELISA assay of paragraph G above even after heating for 3 min at 100° C. in PBS, after treatment with collagenase for 2 hrs at 37° C. in 0.1M Tris, PH 7.4,5 mM $CaCl_2$, 0.02 mM PMSF with a ratio of collagenase to protein of 400 units/mg protein, and after treatment with trypsin for 2 hrs at 37° C. in 50 mM Tris, PH 7.4, 10 mM $CaCl_2$ with a ratio of trypsin to protein of 100 units/mg of protein. However, the protein lost activity after treatment for 1 hr at room temperature in PBS containing 5 mM dithiothreitol (DTT), which would effect reduction of disulfide linkages. Similarly, SDS treatment or fractionation on SDS-PAGE resulted in inactivation of the protein, presumably due to denaturation or complexing by the SDS. The partial amino acid composition of the CIF-A is shown in Table 1.

TABLE 1

| Amino Acid | Mols/100 Mols Recovered |
|---|---|
| Asp | 9.2 |
| Glu | 9.2 |
| Ser | 7.0 |
| His | 2.7 |
| Gly | 16.5 |
| Thr | 2.7 |
| Arg | 5.9 |
| Ala | 6.6 |
| Tyr | 3.2 |
| Met | 0.0 |
| Val | 7.5 |
| Phe | 3.0 |
| Ile | 3.9 |
| Leu | 8.6 |
| Lys | 13.9 |
| Pro | ND |
| Cys | ND |
| Trp | ND |

Amino acid sequence analysis of the protein of peak A by the ninhydrin method showed that is has the following single N-terminal sequence:

```
1                   5                   10
Ala—Leu—Asp—Thr—Asn—Tyr—Cys—Phe—Ser(Ser)Thr—

                15                  20
—Glu—Lys—Asn—Cys—Cys—Val—Arg—Gln—Leu—Tyr—

                25                  30
—Ile—Asp—Phe—Arg—Lys—Asp—Leu—Gly—Trp—.
```

( ) = suspected

This N-terminal sequence is identical to that reported for human placenta-derived TGF-β.

CIF-B had a slightly different molecular weight (26,000) as measured by the same procedure. This difference may be caused by the procedure. Accordingly, both proteins are considered to have a molecular weight of approximately 26,000 daltons as measured by SDS-PAGE. On reduction, CIF-B showed a single band at approximately 14,200 daltons indicating that it, too, is probably a homodimer. It has the amino acid composition set forth in Table 2.

TABLE 2

| Amino Acid | Mols/100 Mols Recovered |
|---|---|
| Asp | 12.0 |
| Glu | 8.5 |
| Ser | 10.6 |
| His | 0.9 |
| Gly | 22.0 |
| Thr | 0.0 |
| Arg | 4.3 |
| Ala | 6.7 |
| Tyr | 1.9 |
| Met | 0.0 |
| Val | 2.4 |
| Phe | 3.0 |
| Ile | 2.2 |
| Leu | 8.2 |
| Lys | 17.3 |
| Pro | ND |
| Cys | ND |
| Trp | ND |

Amino acid sequence analysis indicated CIF-B has a single N-terminal sequence as follows:

```
1                   5                   10
Ala—Leu—Asp—Ala—Ala—Tyr—Cys—Phe—Arg—Asn—Val—

                15                  20
—Gln—Asp—Asn—(Cys—Cys)—Leu—Arg—Pro—Leu—Tyr—

                    25                  30
—Ile—Asp—Phe—Lys—Arg—Asp—Leu—Gly—Trp—.
```

Figure 7:
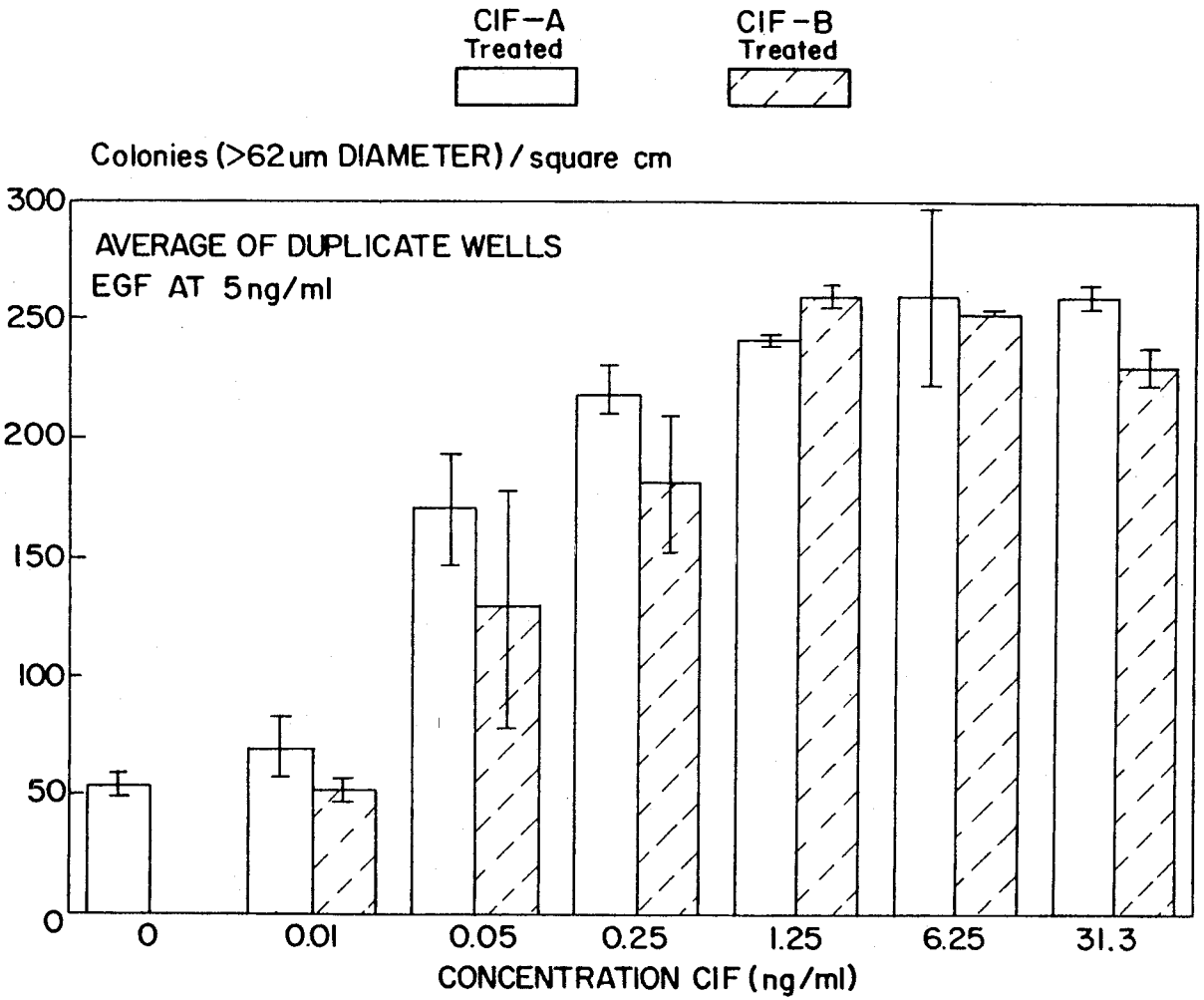
FIG. 7 is a graph of the results of the TGF-$\beta$ assays described in section I of the example, infra.

Its other properties, as qualitatively assessed, were similar to those set forth above for CIF-A. I. Assay for TGF-$\beta$ Activity CIF-A and CIF-B were tested in the TGF-$\beta$ bioassay. This assay determines the ability of a polypeptide to induce anchorage-independent growth in non-neoplastic normal rat kidney (NRK) fibroblasts by measuring the formation of colonies of cells in soft agar. The results of the assays are shown in FIG. 7. As depicted, both proteins exhibit a clear dose-response in the assay and require the presence of an activating agent (EGF) to be active. The levels of activity are comparable to the reported levels of activity of human platelet/human placenta/bovine kidney-derived TGF-$\beta$. As used herein the term "TGF-$\beta$ activity" means that a material is active in the above-described assay.

J. In Vivo Cartilage Induction with Co-factors

1. Formation

A collagenous carrier was prepared by mixing collagen in solution (CIS, 1–3 mg protein/ml; sold by Collagen Corporation under the trademark VITROGEN 100® with bone collagen powder (BCP, lyophilized solids from bone collagen) to give a minimal final concentration of 10% collagen from CIS. The 28 Kd or 36 Kd co-factors of $\pi$ E were formulated with CIF-A and CIF-B and the carrier. CIF-A and CIF-B were present in a weight ratio of 2:1. The weight ratio of CIF to carrier was 1:1200, 1:4500, 1:6000, 1:8000, or 1:20000. The formulations were stirred for 1–2 hr at 4° C. and either directly lyophilized or dialyzed against water and lyophilized. Chondrogenic combinations of CIF-A/CIF-B and these co-factors are not part of the present invention and are the subject of a separate, commonly owned U.S. patent application. They are included herein to illustrate the in vivo chondrogenic activity of CIF-A and CIF-B.

2. Biological Assays of Formulation of $\pi$ H

Implantation. The lyophilized formulations were rehydrated with two parts by weight of cold sterile water and mixed to form a homogeneous paste. The rehydrated material was formed into compact pellets (80–100 mg wet weight). The pellets were implanted subcutaneously in the ventral thoracic region of young male rats. Each rat received bilateral implants. The explants were recovered at 14 days post implantation and evaluated histologically and biochemically.

Histological Evaluation. Explants were fixed in 10% neutral formalin and paraffin embedded by routine methods. Sections were subsequently stained with either hemotoxylin-eosin or with Gomori trichome.

Biochemical Assays. The explants were split in half, their wet weight determined, and frozen at −80° C. until processed. The samples were first extracted and assayed for alkaline phosphate activity and subsequently extracted and assayed for cartilage-specific proteoglycans.

Results. Histological evaluations showed that the implants induced cartilage growth at the implant site. Evaluations of comparison implants containing only CIF or only co-factor showed no cartilage development. Similarly, in the biochemical assays the implants showed high cartilage PG production whereas the comparison implants did not. Comparison implants containing only CIF in which the CIF to carrier weight ratio was greater than about 1:6000 developed a dense collagenous connective tissue matrix throughout the implant. This ability to promote connective tissue deposition does not appear to require association with any co-factor or activating agent that is required for chondrogenic activity or TGF-$\beta$ activity.

The proteins of the invention are useful in combination with co-factors such as the above described 28 Kd and 36 Kd proteins for inducing cartilage/bone formation for repairing, replacing or augmenting cartilage/bone tissue in animals including humans. Chondrogenically/osteogenically effective amounts of the proteins will normally be formulated with pharmacologically and physiologically acceptable fluid or solid carriers for implantation. The weight ratio of CIF to carrier will typically be in the range of 1:1000 to 1:2000. The implants may be placed at a predetermined site in the patient by conventional surgical techniques including injection when formulated as an injectable. When used to promote connective tissue deposition the CIF is combined in effective amounts with carriers conventionally used for implantation. When collagen carrier is used, it appears from the tests reported above that CIF:carrier weight ratios greater than about 1:6000 are required. The amount of CIF may vary when it is combined with other carriers.

The CIFs of the invention may also be used in the same manner as TGF-$\beta$ to promote (provoke and sustain) non-species specific cellular proliferation. In such application the proteins are normally combined in approximately stoichiometric proportions with a TGF-62 activating agent such as an EGF or a TGF-$\alpha$. Clinical applications of the cell proliferation activity of these compositions include topical administration for burn or wound healing or tissue repair. In such uses the proteins and activating agent will be formulated in amounts sufficient to induce soft tissue cell proliferation with pharmaceutically acceptable carriers that are adapted for the particular mode of administration. Topical dosage forms will typically be formulated as sprays, gels, ointments, or salves, implants will be formulated as injectables. Systemic dosage forms may be formulated for enteral administration (e.g. liquids, pills, tablets) or for parenteral injection. The dosages used in such applications cannot be specified because of the nature of all proliferation activity and the variability in wounds and other traumata.

The CIFs may also be useful for treating bone deficiencies such as osteoporosis and osteopetrosis, systemically. For such treatment the CIFs will be formulated in therapeutically effective amounts with injectable carriers and administered parenterally to the patient.

The ability of the CIFs to withstand treatment with trypsin without losing activity may make it possible to isolate them from demineralized bone powder by means of enzymatic digestion. In such a process the demineralized bone powder is digested with an aqueous solution of trypsin and/or other proteases that do not degrade the proteins of interest under conditions at which such enzymes are active. This treatment digests the majority of other protein components in the powder. The proteins of interest may be purified from the resulting digest using one or more of the fractionation techniques described above (gel filtration, ion exchange chromatography, RP-HPLC or nondenaturing gel electrophoresis). Depending upon the extent to which the proteins of interest are released from the bone matrix and not complexed with other materials, use of solubilizing agents may be avoided. In this regard the pure CIFs are substantially soluble in water.

We claim:

1. A composition for promoting proliferation of normal animal cells comprising:

(a) a polypeptide that:

(i) is active in the TGF-$\beta$ assay; and (ii) is a dimer having a molecular weight of approximately 26,000 daltons as determined by SDS-PAGE, whose chains each have the following N-terminal sequence: Ala-Leu-Asp-Ala-Ala-Tyr-Cys-Phe-Arq-Asn-Val-Gln-Asp-Asn-Cys-Cys-Leu-Arg-Pro-Leu-Tyr-Ile-Asp-Phe-Lys-Arg-Asp-Leu-Gly-Trp-;

a TGF-$\beta$ activating agent; and a pharmaceutically acceptable carrier, said polypeptide and activating agent being present in amounts that promote normal cell proliferation.

2. The composition of claim 1 wherein the activating agent is an EGF or a TGF-$\alpha$.

3. A composition for promoting connective tissue deposition comprising:

(a) an effective amount of a polypeptide that (i) is found in mammalian bone;

(ii) is active in the TGF-$\beta$ assay;

(iii) is a co-factor for inducing cartilage formation in vivo;

(iv) is a dimer having an approximate molecular weight of 26,000 daltons as determined by SDS-PAGE; and (v) is free of effective amounts of TGF-$\beta$ activating agent or chondrogenic co-factor; and (b) a pharmaceutically acceptable carrier.

4. A composition for promoting connective tissue depositon comprising:

(a) an effective amount of a polypeptide that (i) is active in the TGF-$\beta$ assay;

(ii) is a dimer having a molecular weight of approximately 26,000 daltons as determined by SDS-PAGE, whose chains each have the following N-terminal sequence: Ala-Leu-Asp-Ala-Ala-Tyr-Cys-Phe-Arg-Asn-Val-Gln-Asp-Asn-Cys-Cys-Leu-Arg-Pro-Leu-Tyr-Ile-Asp-Phe-Lys-Arg-Asp-Leu-Gly-Trp-; and (iii) is free of effective amount of TGF-$\beta$ activating agent or chondrogenic co-factor; and (b) a pharmaceutically acceptable carrier.

*5. A composition for promoting proliferation of normal animal cells comprising:*

*(a) a polypeptide that:*

*(i) is active in the TGF-$\beta$ assay; and*

*(ii) is a dimer having a molecular weight of approximately 26,000 daltons as determined by SDS-PAGE, whose chains each have the following N-terminal sequence: Ala-Leu-Asp-Ala-Ala-Ty r-Cys-Phe-Arq-Asn-Val-Gin-Asp-Asn-Cys-Cys-Leu-Arg-Pro-Leu-Tyr-Ile-Asp-Phe-Lys-Arg-Asp-Leu-Gly-Trp-; and*

*(b) a pharmaceutically acceptable carrier, said polypeptide being present in an amount that promotes normal cell proliferation.*

* * * * *

UNITED STATES PATENT AND TRADEMARK OFFICE

CERTIFICATE OF CORRECTION

PATENT NO. : RE. 34,090

DATED : Oct. 6, 1992

INVENTOR(S) : Saeid Seyedin, Thomas Thomas, Hanne Bentz, Larry Ellingsworth, Rosa Armstrong It is certified that error appears in the above-identified patent and that said Letters Patent is hereby corrected as shown below:

In Column 2, line 24, "RGF-$\beta$" should read --TGF-$\beta$--;

In Column 2, line 43, "bond" should read --bone--;

In Column 3, line 55, "it its" should read --in its--;

In Column 6, line 26, insert a carriage return immediately before "E.";

In Column 6, line 28, "$\pi$" should read --¶--;

In Column 6, line 52, insert a carriage return immediately before "F.";

In Column 7, line 61, insert a carriage return immediately before "H.";

In Column 9, line 34, insert a carriage return immediately before "I.";

In Column 9, line 58, "$\pi$" should read --¶--;

In column 10, line 60, "TGF-62" should read --TGF-$\beta$--;

In Column 12, line 20, "depositon" should read --deposition--.

UNITED STATES PATENT AND TRADEMARK OFFICE

CERTIFICATE OF CORRECTION

PATENT NO. : RE. 34,090
DATED : October 6, 1992
INVENTOR(S) : Saeid Seyedin, et al.

It is certified that error appears in the above-indentified patent and that said Letters Patent is hereby corrected as shown below:

Column 12, line 41, "-Arq-" should read --Arg--.

Signed and Sealed this

Thirtieth Day of May, 1995

*Attest:*

Bruce Lehman

BRUCE LEHMAN

*Attesting Officer*

*Commissioner of Patents and Trademarks*